(12) United States Patent
Chen et al.

(10) Patent No.: US 8,834,447 B2
(45) Date of Patent: Sep. 16, 2014

(54) TRANSDERMAL DRUG DELIVERY PATCH AND METHOD OF CONTROLLING DRUG RELEASE OF THE SAME BY NEAR-IR

(75) Inventors: Mei-Chin Chen, Tainan (TW);
Dong-Hwang Chen, Tainan (TW);
Kuan-Wen Wang, Changhua (TW);
Bo-Hung Lai, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/215,587

(22) Filed: Aug. 23, 2011

(65) Prior Publication Data
US 2012/0283695 A1 Nov. 8, 2012

(30) Foreign Application Priority Data

May 2, 2011 (TW) .............................. 100115364 A

(51) Int. Cl.
| | |
|---|---|
| *B82Y 5/00* | (2011.01) |
| *A61K 9/00* | (2006.01) |
| *A61M 37/00* | (2006.01) |
| *A61K 31/7088* | (2006.01) |
| *A61K 31/715* | (2006.01) |
| *A61K 9/51* | (2006.01) |

(52) U.S. Cl.
CPC ................ *B82Y 5/00* (2013.01); *A61K 9/0021* (2013.01); *A61M 37/0015* (2013.01); *A61M 2037/0053* (2013.01); *A61M 2037/0046* (2013.01); *A61K 31/7088* (2013.01); *A61M 2037/0061* (2013.01); *A61M 2037/0023* (2013.01); *A61K 31/715* (2013.01); *A61K 9/5115* (2013.01)
USPC ............................ 604/506; 424/184; 424/443

(58) Field of Classification Search
CPC .. A61M 37/0015; B82Y 5/00; A61K 51/1244
USPC ................................. 424/449, 184.1; 604/506
See application file for complete search history.

(56) References Cited

U.S. PATENT DOCUMENTS 5,879,326 A * 3/1999 Godshall et al. ............... 604/506
2011/0021970 A1 * 1/2011 Vo-Dinh et al. .................. 604/20

FOREIGN PATENT DOCUMENTS

| CN | 101848702 A | 9/2010 |
|---|---|---|
| TW | 201105379 A1 | 2/2011 |
| WO | WO2008/070538 A2 * | 11/2007 |

OTHER PUBLICATIONS

Holbrook et al., "Regional Diffrences in the Thickness of Human Stratum Corneum: An Ultrastructureal Analysis", J. Inv. Derm., vol. 62(4) p. 415-422, 1974 by Williams & Wilkins Co.*
Mark R Prausnitz, Robert Langer; Transdermal drug delivery; Nature Biotechnology, vol. 26, No. 11, 1261-1268, Nov. 2008 (2008 Nature Publishing Group http://www.nature.com/naturebiotechnology).
Jeong W. Lee, Jung-Hwan Park, Mark R. Prausnitz; Dissolving microneedles for transdermal drug delivery; Biomaterials 29 (2008), 2113-2124 (Elsevier, www.elsevier.com/locate/biomaterials).
Sean P Sullivan, Niren Murthy, Mark R. Prausnitz; Minimally Invasive Protein Delivery with Rapidly Dissolving Polymer Microneedles; Advanced Materials, 2008, 20, 933-938 (2008 Wiley-VCH Verlag GmbH & Co. KGaA, Weinheim).

* cited by examiner

*Primary Examiner* — Richard Schnizer
*Assistant Examiner* — Yanzhi Zhang
(74) *Attorney, Agent, or Firm* — Muncy, Geissler, Olds & Lowe, P.C.

(57) ABSTRACT

A transdermal drug delivery patch and a method of controlling the drug release of the transdermal drug delivery patch by near-IR are disclosed. The transdermal drug delivery patch comprises a substrate, carriers and drugs. The drugs are encapsulated in the carriers, and the carriers having the drugs are disposed on a surface of the substrate. The carriers are formed of biodegradable polymers, and nano-particles with a photothermal conversion effect are loaded in the carrier. When the carriers are punctured into the skin and the nano-particles in the carrier absorb the near-IR, the near-IR is converted into heat by the nano-particles to melt the carrier and thus releasing the drugs encapsulated in the carrier into the skin. Accordingly, the speed of releasing the drugs encapsulated in the carrier can be controlled accurately by the near-IR.

20 Claims, 23 Drawing Sheets

TRANSDERMAL DRUG DELIVERY PATCH AND METHOD OF CONTROLLING DRUG RELEASE OF THE SAME BY NEAR-IR

FIELD OF THE INVENTION

This application claims priority from Taiwan Patent Application No. 100115364, filed on May 2, 2011, the contents of which are hereby incorporated by reference in their entirety for all purposes.

The present invention relates to a drug delivery patch and a drug release method thereof, in particular to a transdermal drug delivery patch and a method of controlling a drug release of the patch by near-IR.

BACKGROUND OF THE INVENTION

Biomolecules, including proteins, peptides and vaccines, make up a large and potent portion of new drugs, and hold great promise for the future of therapeutics. Although oral delivery of these biotherapeutics would be desirable, there is low bioavailability of biomolecules administered by this route due to enzymatic degradation and poor absorption in the GI track, as well as first-pass metabolism of liver. As a result, most biotherapeutics are administered by hypodermic injection, which causes pain or infection, requires to traine personnel and often needs to repeat injections for the patient. Consequently, there exists the need for a minimally invasive, self-administered delivery system for biomolecules.

To address limitations of oral delivery and hypodermic injection, transdemal delivery has been developed to painlessly pierce skin's outer barrier of stratum corneum with the goal to deliver drugs. Transdermal delivery has a variety of advantages compared with the oral delivery. In particular, it is used when there is a significant first-pass effect of the liver that can prematurely metabolize drugs. Transdermal delivery also has advantages over hypodermic injections, which are painful, generate dangerous medical waste and pose the risk of disease transmission by needle re-use. Additionally, the advantage of the transdermal delivery are that it not only crosses the stratum corneum barrier to target dendritic cell in the skin, but dose so using an inexpensive, disposable patch that is simple enough to be suitable for self administration by patients.

The first transdermal system for systemic delivery, a three-day patch that delivers scopolamine to treat motion sickness, was approved for use. A decade later, nicotine patches became the first transdermal blockbuster, raising the profile of transdermal delivery in drugs and for the public in general. Today, there are many transdermal delivery systems for such drugs, such as estraldiol, fentanyl or testosterone, etc. Above descriptions can see in "Prausnitz M. R. et al., Transdermal drug delivery, 2008"; "Lee J. W. et al., Dissolving microneedles for transdermal drug delivery, 2007"; "Kim Y. C. et al., Formulation and coating of microneedles with inactivated influenza virus to improve vaccine stability and immunogenicity, 2009"; and "Sullivan S. P. et al., Minimally invasive protein delivery with rapidly dissolving polymer microneedles, 2008".

However, in various situations, the delivery speed or flux of a variety of reagents (such as the macromolecular or hydrophilic drugs) is limited by the passive transdermal path, resulting in ineffective treatment. The transdermal delivery method can be allowed the drug to be delivered into the body by passive diffusion, or by external energy including electricity (such as an ion introduction method) or ultrasound (such as an ultrasonic penetration method). Although the drug can be delivered through the stratum corneum and epidermis, the delivery speed of the diffusion through the stratum cuticle is usually a limited step. In addition, in order to achieve an effective dose, a variety of compounds require a delivery speed higher than the speed of simple passive transdermal diffusion.

Furthermore, most conventional transdermal drug delivery patches are quick-release carriers. That is, when external energy is applied, the drug encapsulated in the carrier is released immediately, and the release rate thereof can not be regulated precisely. Therefore, how to control the release rate of the drug encapsulated in the carrier by external energy becomes an important issue.

SUMMARY OF THE INVENTION

In view of the aforementioned shortcomings of the prior art, it is a primary objective of the present invention to provide a transdermal drug delivery patch and a method of controlling a drug release of the patch by near-IR, so as to achieve the effect of controlling the release of drugs encapsulated in a carrier by near-IR accurately.

To achieve the objective, the present invention provides a transdermal drug delivery patch comprising a substrate, a carrier and a drug. The drug is encapsulated in the carrier, and the carrier having the drug is disposed on a surface of the substrate. The carrier is formed of biodegradable polymers, and nano-particles with a photothermal conversion effect are loaded in the carrier. When the carrier is punctured into a skin and the nano-particles in the carrier absorb the near-IR, the near-IR is converted into heat by the nano-particles to melt the carrier and thus releasing the drug encapsulated in the carrier into the skin.

In addition, the present invention further provides a method controlling a drug release by near-IR, and the method is applied to said patch. The method comprises the steps of: attaching the carrier of the transdermal drug delivery patch onto a skin to puncture into the skin; using near-IR to irradiate the transdermal drug delivery patch; absorbing the near-IR by the nano-particle in the carrier of the transdermal drug delivery patch, and converting the near-IR into heat; and melting the carrier of the transdermal drug delivery patch by the heat produced by the nano-particle to release the drug encapsulated in the carrier into the skin.

The transdermal drug delivery patch and the method of controlling a drug release of the patch by near-IR in accordance with the present invention have one or more of the following advantages:

(1) The currently developed polymer microneedle patches are quick-release drugs, the drug release speed thereof is primarily determined by the biochemical properties (such as hydrophilicity, hydrophobicity and crystallinity) of polymers, and there is no polymer micro-needle system capable of regulating the drug release speed available yet. The present invention provides a patch for controlling the drug release from a micro-needle carrier accurately by near-IR, and the invention can be applied for diseases that require long-term treatments or medications.

(2) A variety of transdermal drug delivery patches for releasing different dosages can be developed by controlling the intensity, time and frequency of the irradiation of near-IR in accordance with the present invention, so as to achieve the effects of controlling the drug release minimally-invasively, providing an easy control on the time of drug effect, reducing the drug's side effects, and maximizing the treatment effect.

(3) The transdermal drug delivery patch of the present invention is a painless minimally-invasive medical system that integrates the advantages of traditional injections and transdermal patches, uses micron-scale needles to puncture a stratum corneum of human skin without stimulating the nerve system at the dermis, and delivers a macromolecular drug into the skin effectively, such that the drug can be absorbed by capillaries and entered into target tissues or circulated in the whole body.

(4) After the carrier of the transdermal drug delivery patch of the present invention punctures into the skin, the carrier can be degraded or dissolved in human body. Thus, users need not to worry about the cracked carrier remained in the user's body forever, or the problems of using the micro-needle carrier repeatedly on purpose, and disposing used needles.

DESCRIPTION OF THE PREFERRED EMBODIMENTS

The following preferred embodiments are described in details for the purpose of illustrating the present invention, but not intended for limiting the scope of the present invention.

The terminology "transderm" used in the present specification refers to a delivery meaning that a reagent (including a therapeutic agent or an immune activator such as a drug and a vaccine) is delivered to local tissues or a circulation system of the whole body via skin. Overall speaking, the "transderm" is a non-invasive or minimally-invasive drug delivery.

Figure 1:
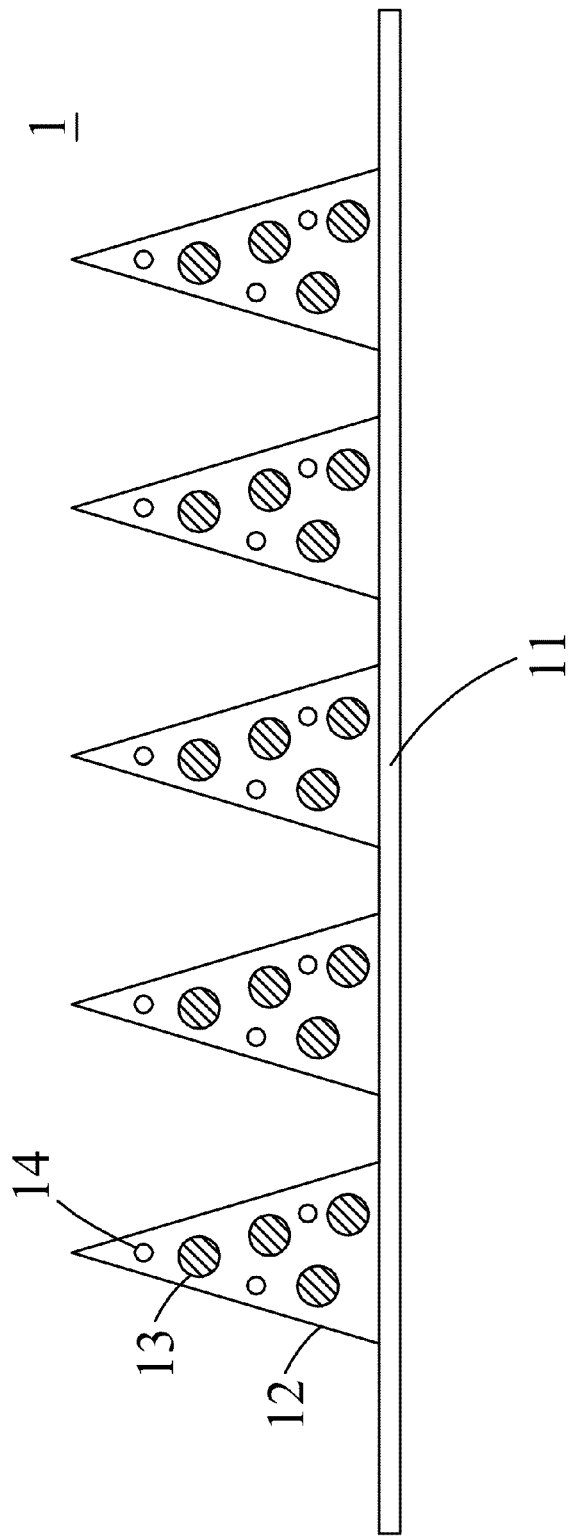
FIG. 1 is a schematic view of a transdermal drug delivery patch in accordance with an embodiment of the present invention.

With reference to FIG. 1 for a schematic view of a transdermal drug delivery patch in accordance with an embodiment of the present invention, the transdermal drug delivery patch 1 comprises a substrate 11, carriers 12 and drugs 13. The drugs 13 are encapsulated into the carrier 12, and the carriers 12 having the drug 13 are disposed on a surface of the substrate 11. The carriers 12 are formed by a biodegradable polymer and include nano-particles 14 with photothermal conversion effect for converting light into heat.

If the carriers 12 of the transdermal drug delivery patch 1 is attached onto skin, and the nano-particles 14 in the carriers 12 absorb near-IR, the nano-particles 14 can convert the near-IR into heat to melt the carriers 12 and release the drugs 13 encapsulated in the carrier 12 into the skin. Thus, the drugs 13 are absorbed by capillaries and entered into the whole body for circulation.

In order to puncture the carriers 12 into the skin, the carriers 12 have a shape of a micro-needle, a triangular cone, a circular cone, or any shape capable of making the carriers 12 puncture into skin. As to the users, the transdermal drug delivery patch of the present invention is a minimally-invasive drug treatment, so that the heights of the carriers 12 of the present invention cannot be too large. If the heights of carriers 12 are too large, the user may feel significant pain. Preferably, the heights of the carriers 12 fall within a range of 50-1200 μm.

After the nano-particles 14 absorb the near-IR, the near-IR is converted into heat to melt the carrier 12, so that the melted and collapsed carriers 12 remain in the skin. Therefore, the composition of the carriers 12 is very important to the present invention. In the present invention, the carriers 12 are made of a bio-degradable polymer, preferably a biodegradable polymer with a low melting point (approximately 35-70) such as polycaprolactone (PCL), gelatin, methylcellulose or polyethylene oxide (PEO).

The nano-particles 14 with the photothermal conversion effect for converting light into heat can be a metal nano-particle such as a gold nano-particle, a gold nanorod, gold and silver nano hollow spheres, or a germanium (Ge) nano-particle. The nano-particle also can be a single-walled carbon nanotube or a lanthanum hexaboride ($LaB_6$) nano-particle.

The substrate 11 includes an elastic non-woven fabric, a hydrogel glue patch, a bio-fiber or any combination of the above. The substrate 11 can be made of the same biodegradable polymer of the carrier such as polycaprolactone, gelatin, methyl cellulose or polyethylene glycol.

Figure 2:
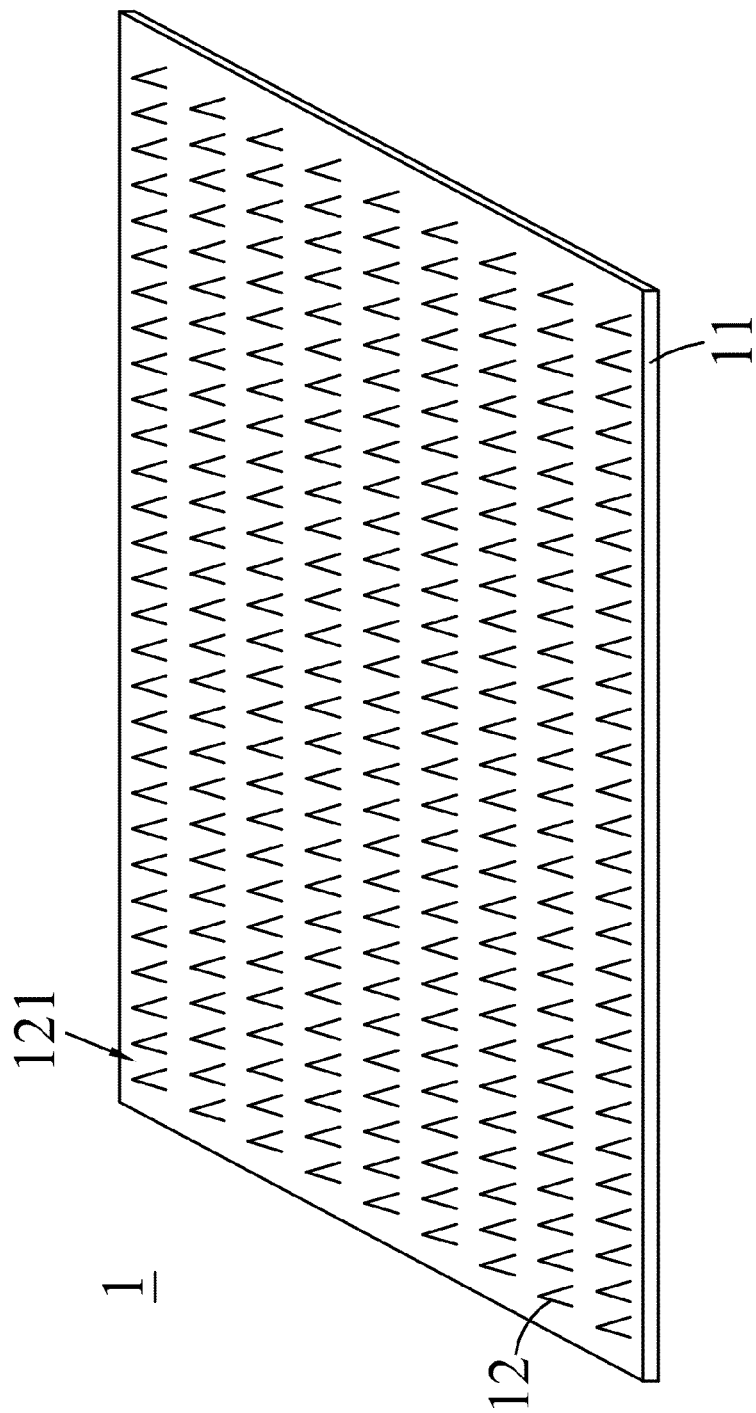
FIG. 2 is a perspective view of a transdermal drug delivery patch in accordance with an embodiment of the present invention.

With reference to FIG. 2 for a perspective view of a transdermal drug delivery patch in accordance with an embodiment of the present invention, the transdermal drug delivery patch 1 comprises a substrate 11, carriers 12 and drugs (not shown). The drugs are encapsulated in the carriers 12, and the carriers having the drug 12 are disposed on a surface of the substrate 11. The carriers 12 are made of a biodegradable polymer and include nano-particles (not shown) with photothermal conversion effect for converting light into heat. In the present embodiment, the carrier 12 is a structure of a micro-needle array 121. When the transdermal drug delivery patch 1 is attached onto human skin, the carriers 12 with the structure of the micro-needle array 121 will puncture the stratum corneum of the skin. After the carrier 12 with the structure of the micro-needle array 121 punctured into the skin is irradiated by near-IR, the carriers 12 absorb the near-IR through its nano-particles and covert the near-IR into heat to melt the carriers 12 to further release the drugs encapsulated in the carriers. Accordingly, the drug will be diffused into human body and absorbed by tissues. Since the carriers 12 are composed of the biodegradable polymer, the carriers 12 can be decomposed in human skin naturally or absorbed by human body, and will not affect the user's normal metabolic function.

The manufacturing method of the transdermal drug delivery patch in accordance with the present invention will be described below to allow persons ordinarily skilled in the art to implement the present invention. However, all described by the following use of materials and parameters including concentration, content, and reaction time are not as limited, and modifications and variations could be made thereto by those skilled in the art without departing from the scope and spirit of the invention set forth.

Figure 3:
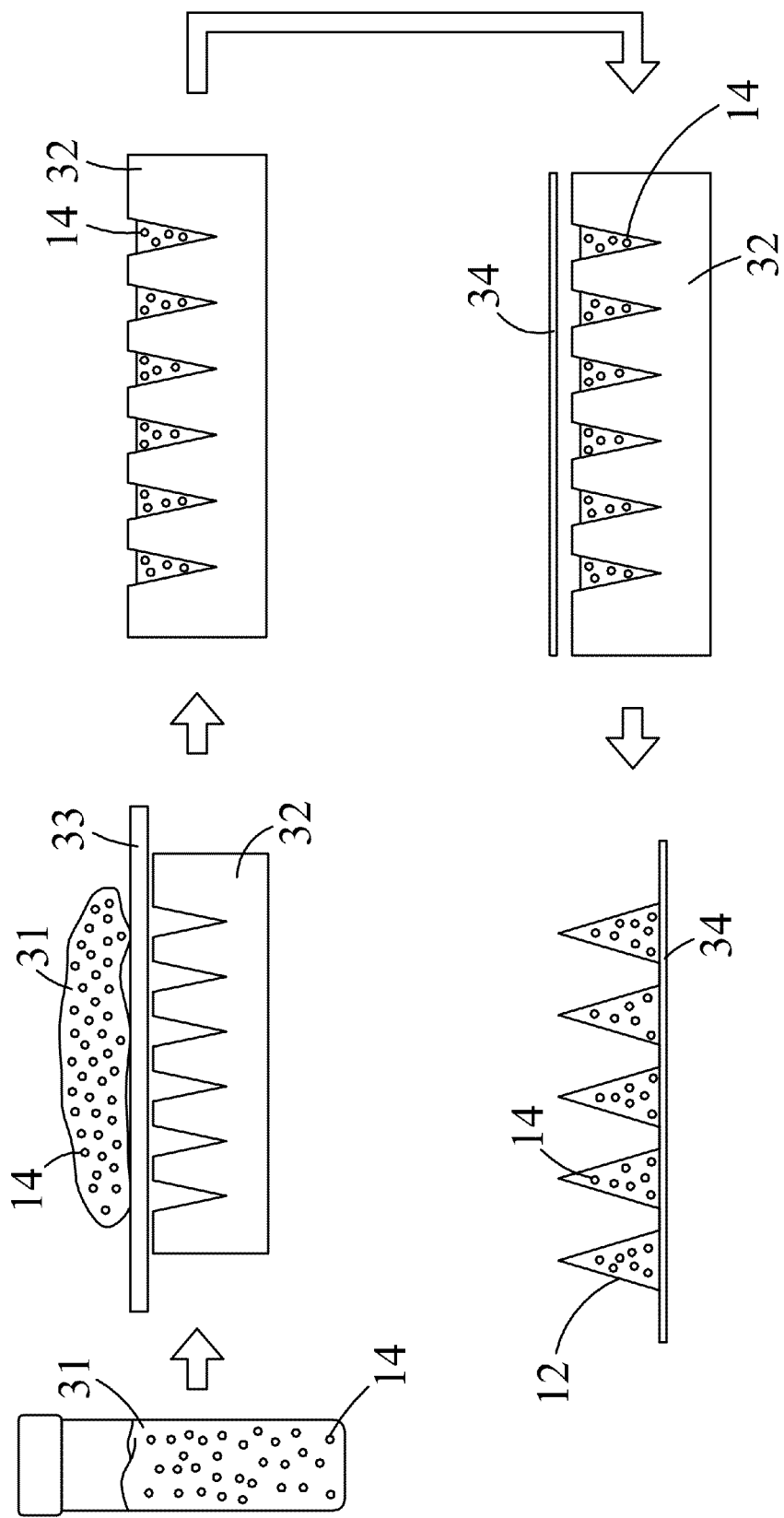
FIG. 3 is a schematic view of a method of manufacturing a transdermal drug delivery patch in accordance with a embodiment of the present invention.

With reference to FIG. 3 for a schematic view of a method of manufacturing a transdermal drug delivery patch in accordance with an embodiment of the present invention. As shown, firstly, a 25% w/v PCL solution 31 is prepared by adding 4 g PCL to acetone, followed by heating at 70 and stirring, until a homogeneous various solution is formed. In addition, $LaB_6$ nano-particles with photothermal conversion effect are used in the present embodiment. 2 ml of $LaB_6$ (16 mg/ml) nano-particles in isopropanol are then added to the PCL solution 31, followed by sonication for 30 minutes for effective dispersion of $LaB_6$ in the PCL solution. On the other hand, before the molding process, a filter paper (Whatman, No. 1441-047) 33 is put on the polydimethylsiloxane (PDMS) micro-needle mold 32 and 1 ml of the PCL solution 31 containing $LaB_6$ nano-particles 14 is added on it. Such solution covered mold is then put in a conical centrifuge tube and centrifuged in a 90° angled rotor (Hermle, Z326K, not limited thereto) at 4500 rpm and 30° C. for 1.5 hr to fill the micro-needle mold cavities.

After centrifugation, the excess mixed solution and filter paper 33 on the mold are removed, and the filled mold is placed into an oven to dry at the temperature of approximately 37 for up to 5 hours to form micro-needle carriers 12. In order to attach the carriers 12 onto skin, a substrate such as an elastic non-woven fabric, a hydrogel glue patch, a bio-fiber or a biodegradable polymer composed of the same material of the carrier is disposed on the bottom surfaces of the carriers. When a pressure is applied, the pressure can press the micro-needle carriers uniformly onto the skin. In the present embodiment, a PCL slice 34 with an appropriate size serving as a substrate can be put into a dried mold and followed by heating in the oven at 70 for 4 hours, so that the PCL slice 34 and the micro-needle carrier 12 are melted and integrated with each other. After that, the micro-needle mold 32 is removed from the oven and cooled to room temperature, and the transdermal drug delivery patch having nano-particles with the photothermal conversion effect in accordance with the present invention can be peeled off from the mold.

In the aforementioned manufacturing method, the mixed solution (which is the polycaprolactone solution 31 containing nano-particles) can be added with drugs. It is noteworthy to point out that the drug release mechanism of the present invention is achieved by near-IR irradiations, and the nano-particles with the photothermal conversion effect are used for heating and melting the carriers, such that the drug encapsulated in the carrier can be released into the skin. Therefore, the present invention is more suitable for thermally stable drugs such as deoxyribonucleic acids (DNA), polysaccharides, and some of the heat resisting vaccines, proteins or chemical synthetic drugs.

Figure 4:
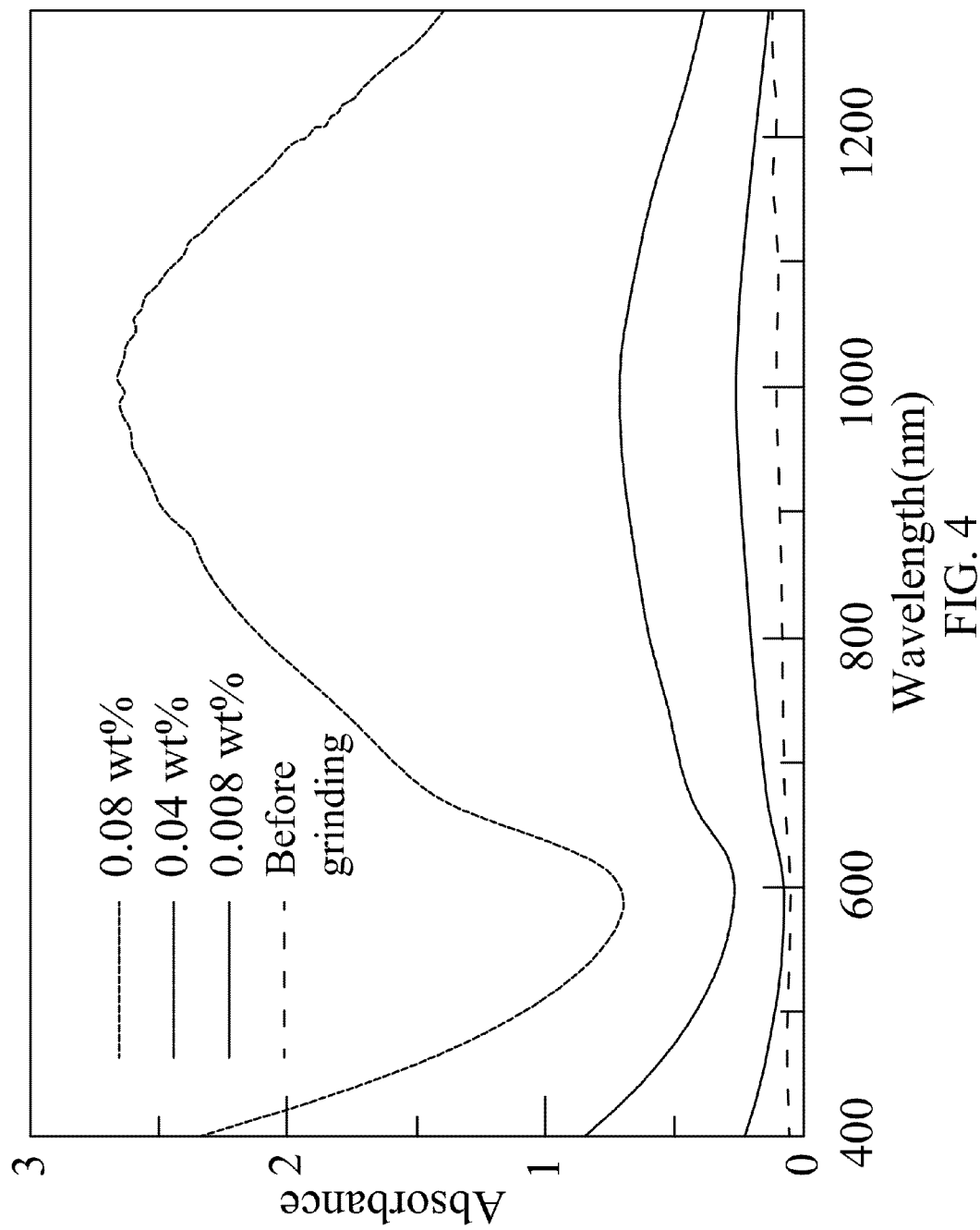
FIG. 4 is an absorption spectrum of lanthanum hexaboride nano-particles of different concentrations.
Figure 5A:
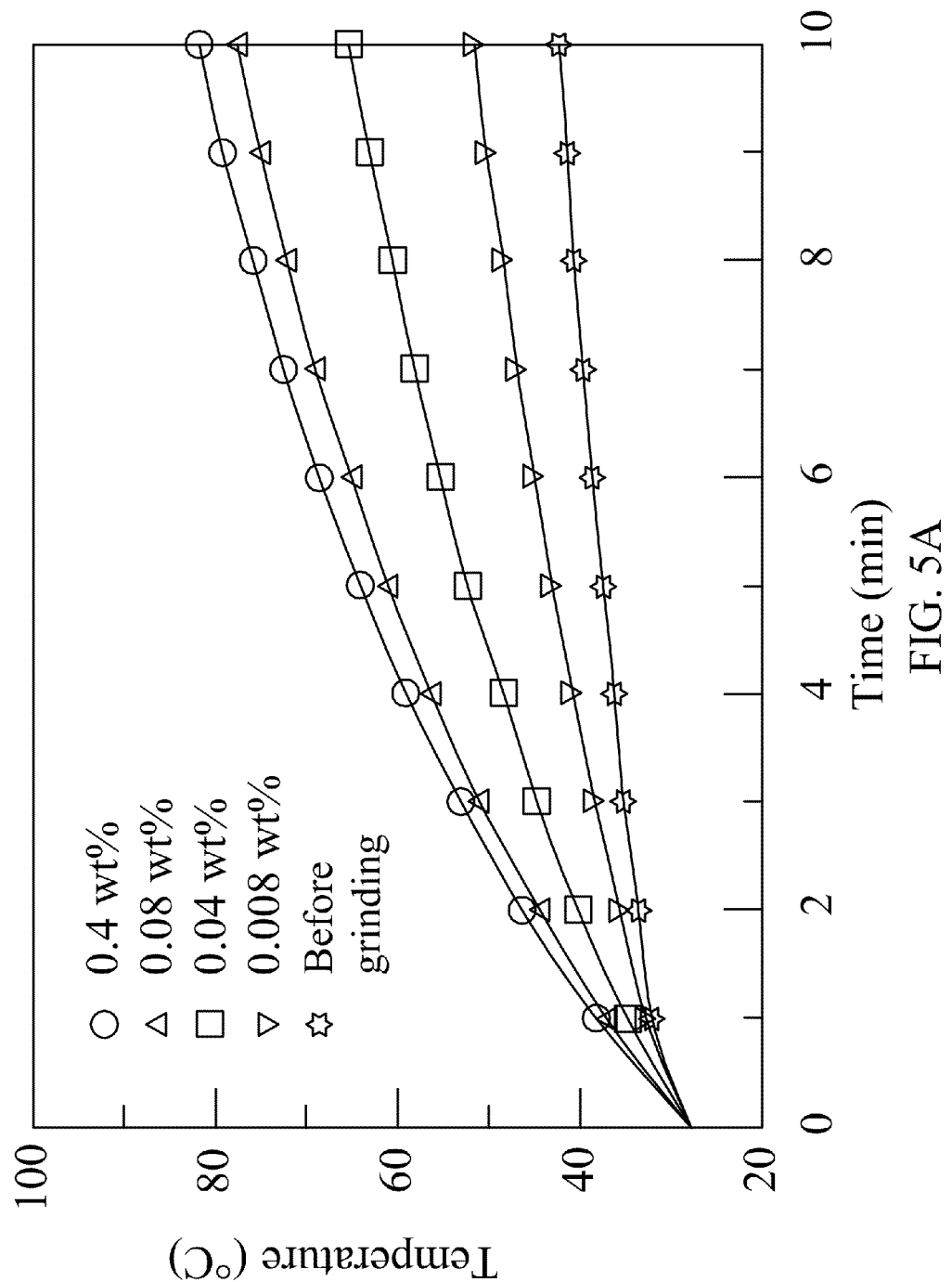
FIG. 5A is a irradiation time versus temperature graph of lanthanum hexaboride nano-particles with different concentrations.
Figure 5B:
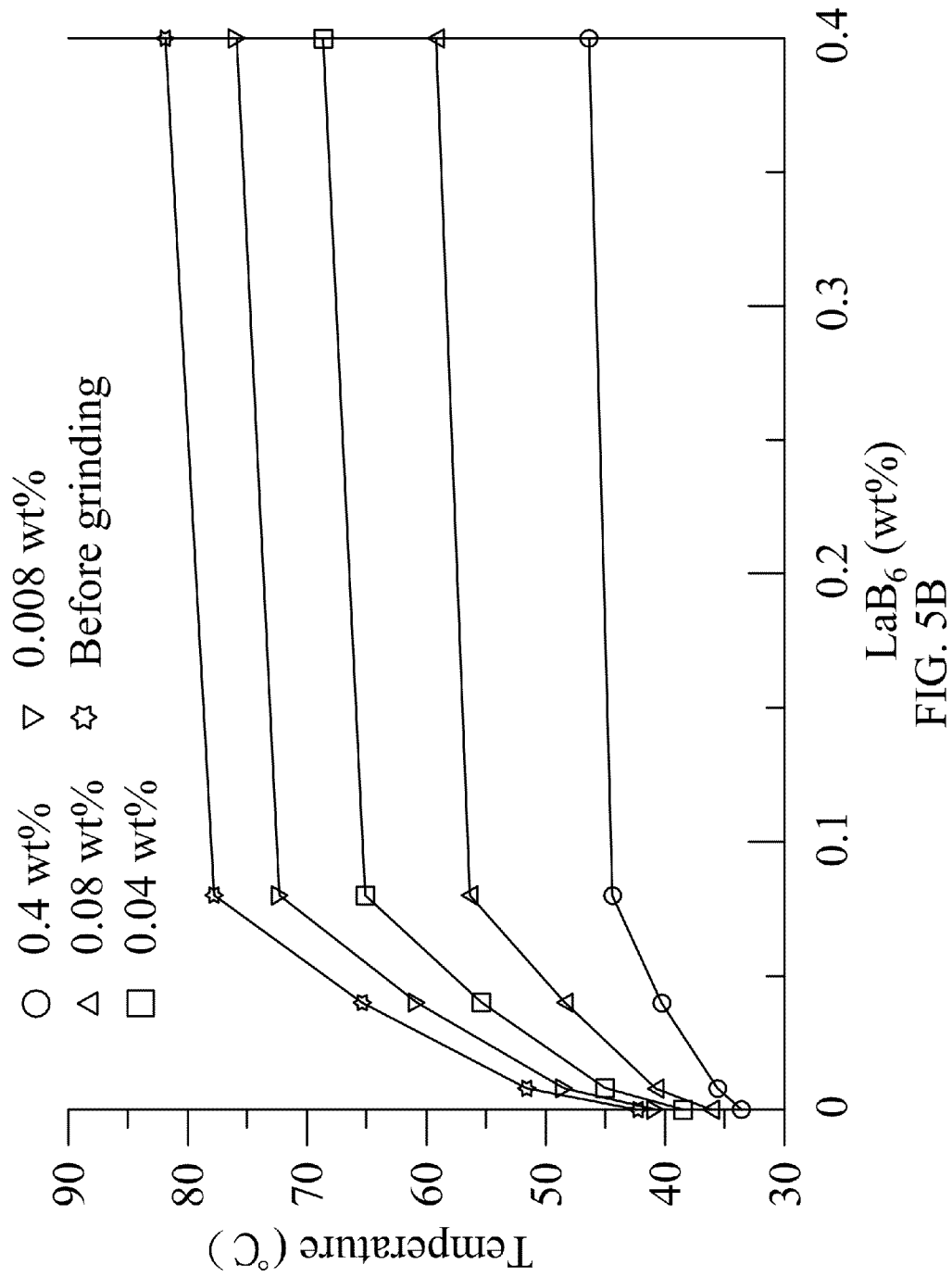
FIG. 5B is a temperature versus concentration graph of lanthanum hexaboride nano-particles.

The $LaB_6$ nano-particles of the present embodiment are nano-particles with a photothermal conversion effect, since the $LaB_6$ nano-particles have free electrons on the surface thereof and can produce a surface plasmon resonance. For the $LaB_6$ nano-particles, the absorption wavelength of the near-IR is approximately 800-1300 nm and the maximum absorption peak is at the wavelength of 1030 nm. Additionally, the absorption wavelength increases with concentration as shown in FIG. 4. To observe the temperature change of the $LaB_6$ nano-particles with different concentrations irradiated by the near-IR, $LaB_6$ nano-particle solutions with different concentrations are irradiated by near-IR (with a wavelength of 808 nm and a power of 820 mW) in this embodiment. With reference to FIG. 5A for a irradiation time versus temperature graph of a $LaB_6$ nano-particle solution with different concentrations, the results show that under the same irradiation time, the higher the concentration is, the faster the temperature rise and the higher the achieved temperature is. With reference to FIG. 5B for a time versus temperature graph of $LaB_6$ nano-particles with different concentrations, the temperature and the concentration have a linear relation in the condition of a low concentration. However, the rising temperature and the concentration do not have the linear relation in the condition of a high concentration, and the temperature rise tends to be increasingly slower. The main cause is due to the influence of the absorption of the $LaB_6$ nano-particles. The Lamber-Beer Law shows that the absorption at a low concentration has a linear relation, and the absorption tends to become slower at a high concentration.

Figure 6A:
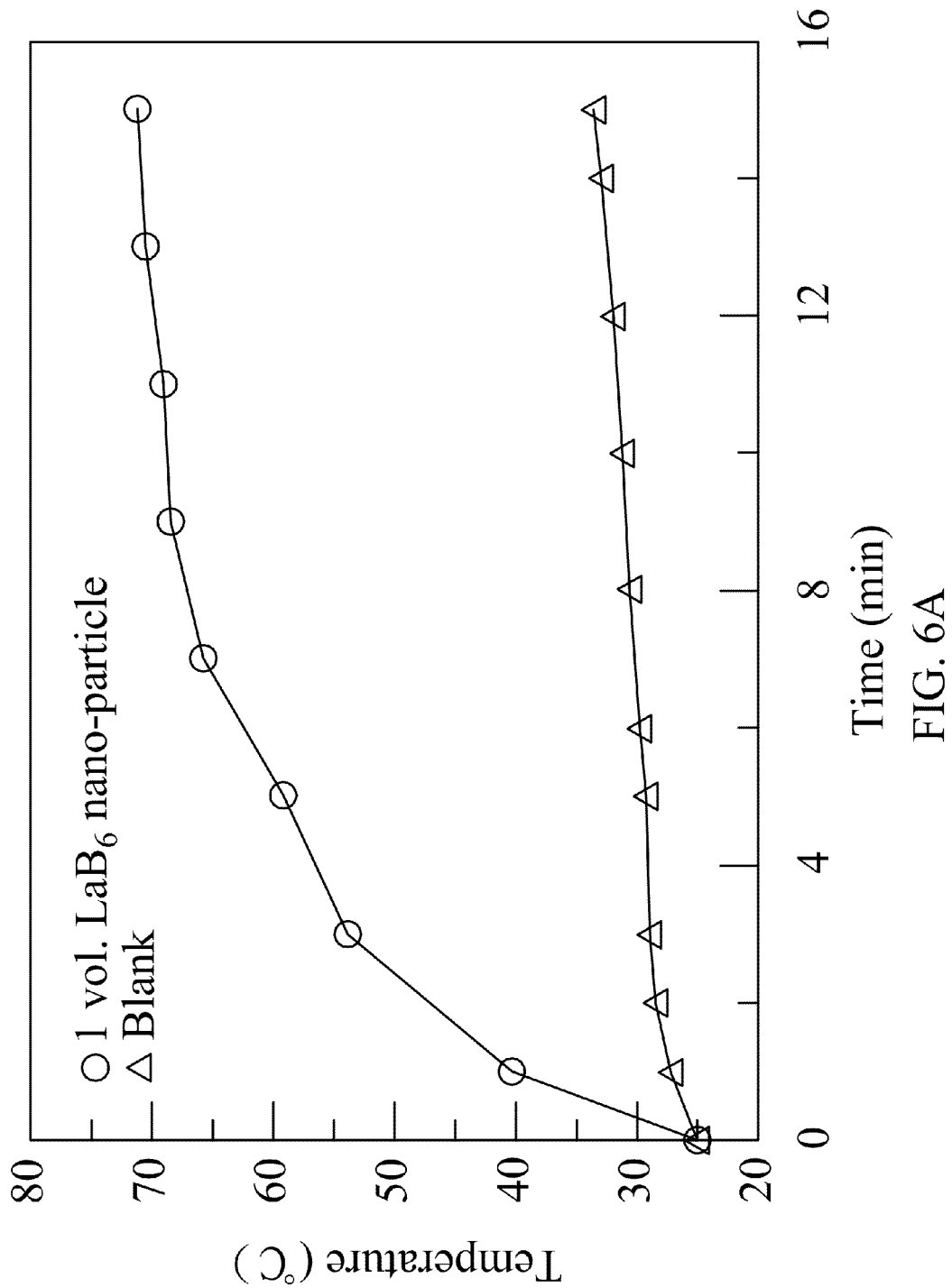
FIG. 6A is a temperature irradiation versus time graph of a lanthanum hexaboride nano-particle solution with a concentration of 1% by volume.
Figure 6B:
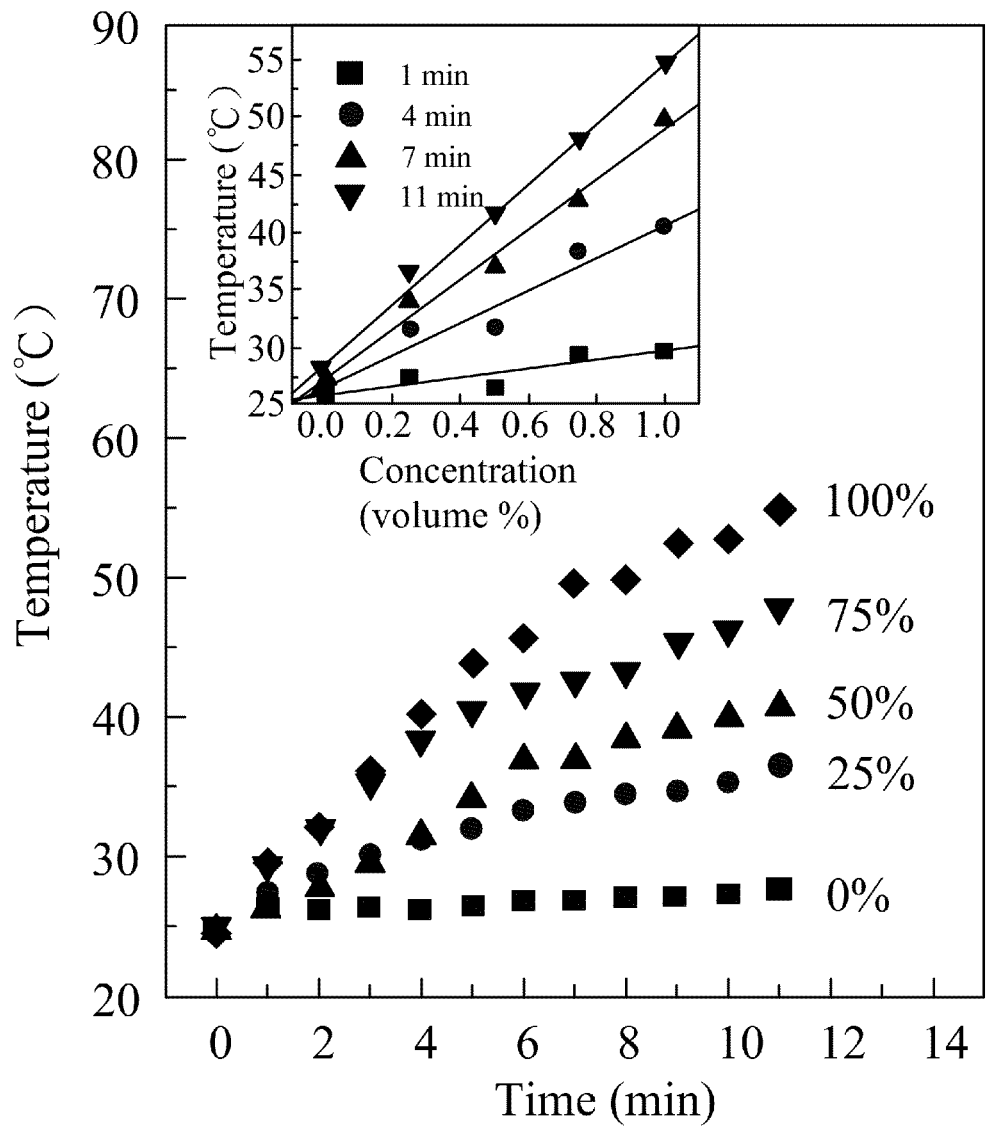
FIG. 6B is a temperature versus irradiation time graph of gold nano-particles with a concentration of 1% by volume.
Figure 7A:
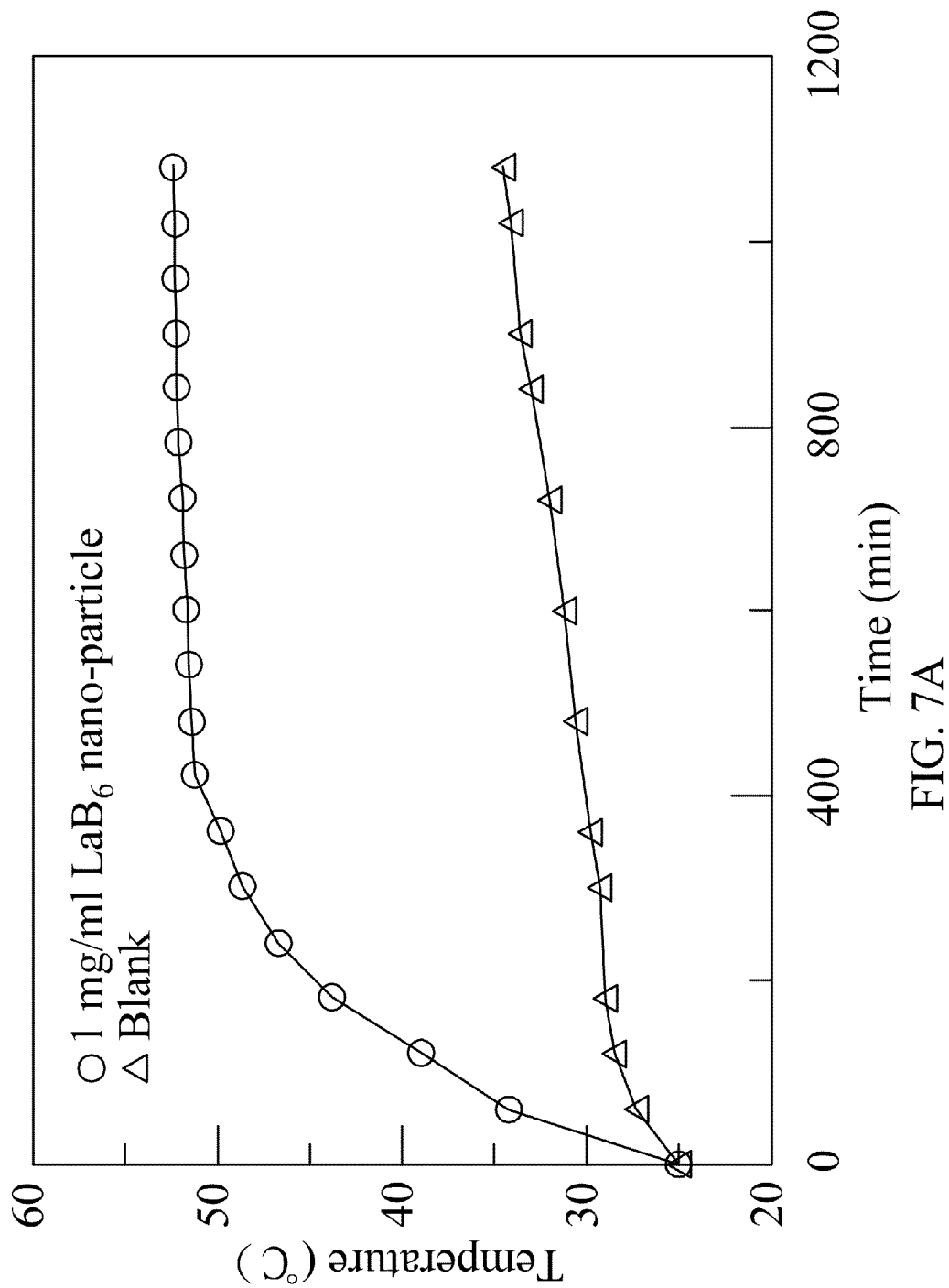
FIG. 7A is a temperature versus irradiation time graph of a lanthanum hexaboride nano-particle solution with a concentration of 1 mg/ml.
Figure 7B:
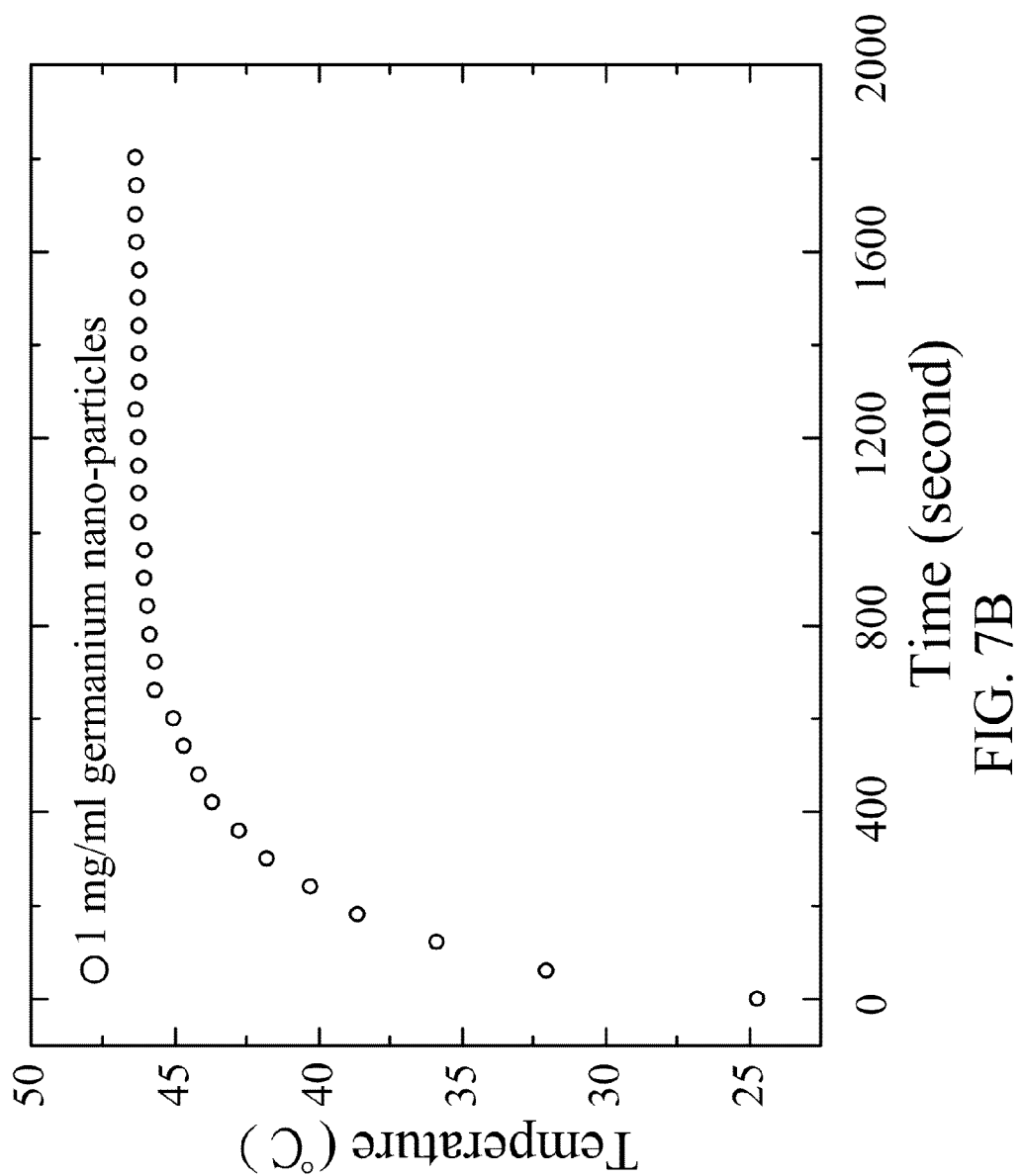
FIG. 7B is a temperature versus irradiation time graph of germanium nano-particles with a concentration of 1 mg/ml.

In addition, the speeds of the temperature rises of the $LaB_6$ nano-particles, the gold nano-particles, and the germanium nano-particles are compared, and the results are shown in FIGS. 6A, 6B, 7A and 7B. With reference to FIGS. 6A and 6B for temperature versus irradiation time graphs of the $LaB_6$ nano-particle solution with a concentration of 1% by volume and the gold nano-particles with a concentration of 1% by volume respectively, the "Δ" in FIG. 6A represents a blank control group (deionized water). In FIG. 6B, after the gold nano-particles are irradiated by the near-IR of 5 $W/cm^2$ for approximately 11 minutes, the temperature rises from 25° C. to 55° C. In FIG. 6A, after the $LaB_6$ nano-particle solution with a concentration of 1% by volume is irradiated by the near-IR of 2.7 $W/cm^2$ for the time as same as irradiating the gold nano-particles, the temperature rises from 25° C. to 69° C. The results show that the speed of temperature rise of the $LaB_6$ nano-particles is greater than that of the gold nano-particles. With reference to FIGS. 7A and 7B for temperature versus irradiation time graphs of the $LaB_6$ nano-particle solution with a concentration of 1 mg/ml and the germanium nano-particles with a concentration of 1 mg/ml respectively, the "Δ" in FIG. 7A represents a blank control group (deionized water). In FIG. 7B, after the germanium nano-particles are irradiated by the near-IR (with a wavelength of 770 nm and a power of 0.9 W), the temperature rises from 25 to 46. In FIG. 7A, the $LaB_6$ nano-particle solution rises from 25° C. to 51° C. The results show that the temperature of both gold nano-particles and germanium nano-particles rises after they are irradiated by the near-IR, and the speed of temperature rise of the $LaB_6$ nano-particles is greater than those of the gold nano-particles and germanium nano-particles.

Figure 8:
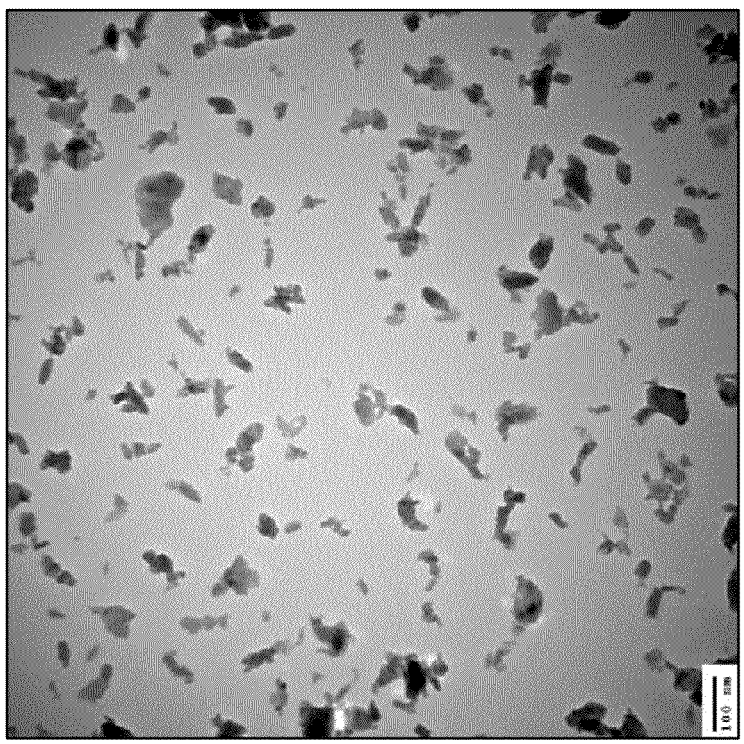
FIG. 8 is a transmission electron microscope (TEM) image of grinded lanthanum hexaboride nano-particles.

In the present embodiment, the $LaB_6$ nano-particles can be manufactured by a wet grinding method. Silicon carbide blades are used to drive a grinding medium, yttrium stabilized zirconia (YSZ) micro-beads, to grind the $LaB_6$ nano-particles, and an isopropyl alcohol solvent is used as a dispersion medium, so as to manufacture the $LaB_6$ nano-particle solution. The result after the grinding process is shown in FIG. 8.

Figure 9:
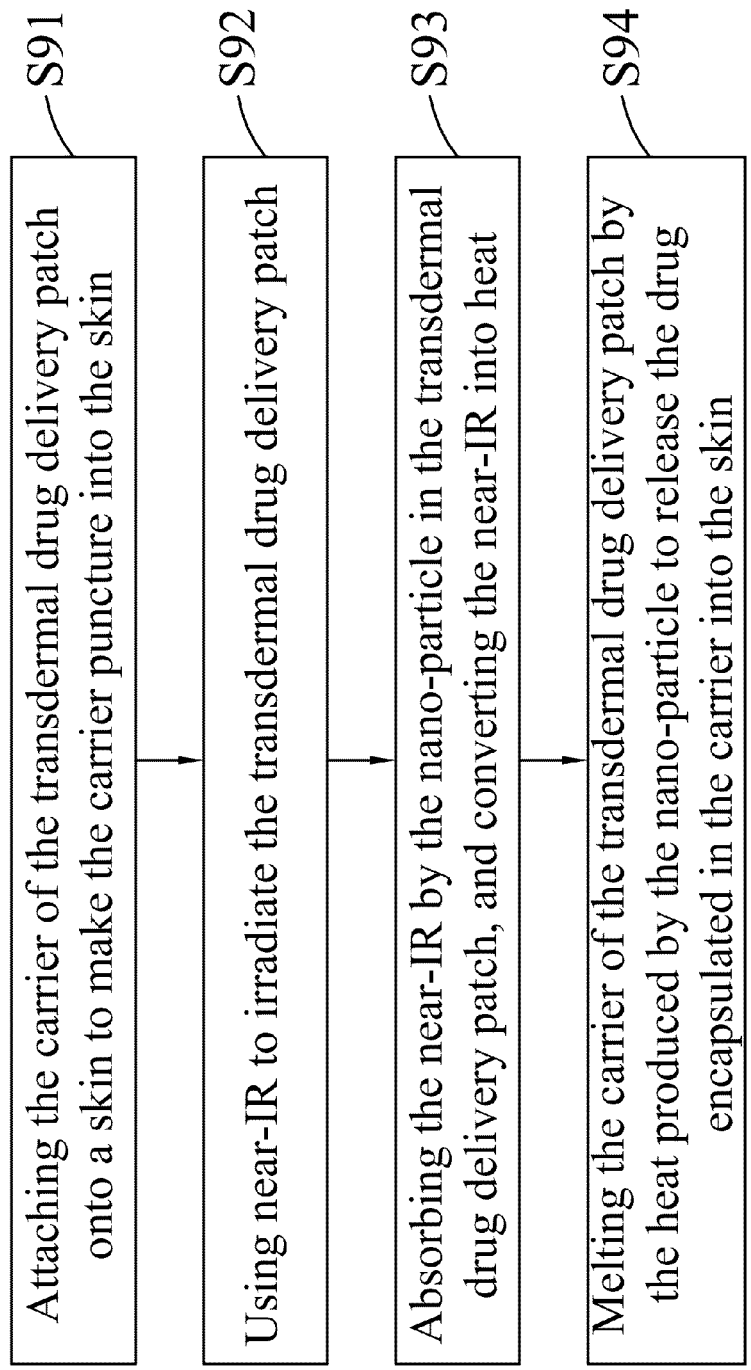
FIG. 9 is a flow chart of a method of controlling a drug release by near-IR in accordance with an embodiment of the present invention.
Figure 10:
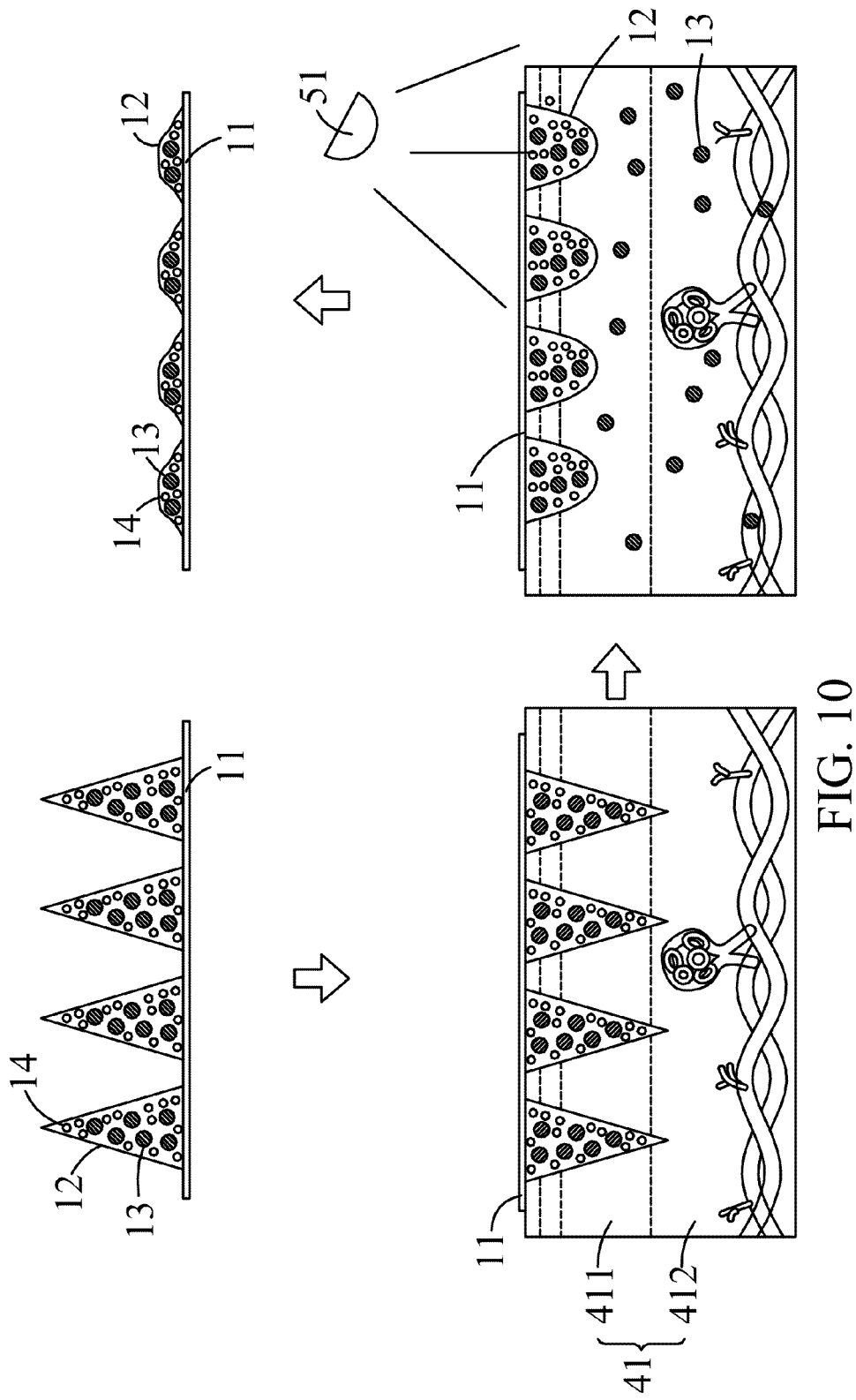
FIG. 10 is a schematic flow chart of a method of controlling a drug release by near-IR in accordance with an embodiment of the present invention.

With reference to FIGS. 9 and 10, FIG. 9 is a flow chart of controlling a drug release by near-IR in accordance with an embodiment, and FIG. 10 is a schematic flow chart of controlling a drug release by near-IR in accordance with an embodiment. The method of the present invention is applied to the aforementioned transdermal drug delivery patch, and the method comprises the following steps. In Step S91, carriers 12 on a surface of a transdermal drug delivery patch 1 is attached onto a skin 41, such that the carriers punctures the epidermis 411 or the dermis 412 of the skin 41. In Step S92, the near-IR 51 is irradiated onto of the transdermal drug delivery patch 1 of the present invention. In Step S93, nano-particles 14 in the transdermal drug delivery patch absorbs the near-IR 51 to convert the near-IR 51 into heat. In Step S94, the heat generated by the nano-particles 14 melts the carriers 12 of the transdermal drug delivery patch to release drugs 13 encapsulated in the carrier 12 into the skin.

The near-IR of the present invention has a wavelength of 650-1300 nm and an irradiation time of approximately 0.1-20 minutes each time. In an embodiment, if the nano-particles of the transdermal drug delivery patch have contents of 0.4-1 wt %, then the wavelength of the near-IR can be 800-900 nm and the power can be 600-800 mW. After the carriers 12 are irradiated for 0.1-60 seconds, the carriers are melted, such that the drugs 13 encapsulated in the carriers can be released into the skin. Therefore, the method of controlling the drug release in accordance with the present invention can achieve the characteristic of controlling the time of drug effect accurately, reducing side effects, and maximizing the treatment effect by controlling the intensity, time and frequency of the near-IR irradiation.

To prove that the drug release of the transdermal drug delivery patch of the present invention can be controlled by near-IR, the following experiment is used to confirm the effect of the present invention. It is noteworthy to point out that the parameters here are provided for the illustration purpose only, but not intended for limiting the scope of the present invention.

Figure 11:
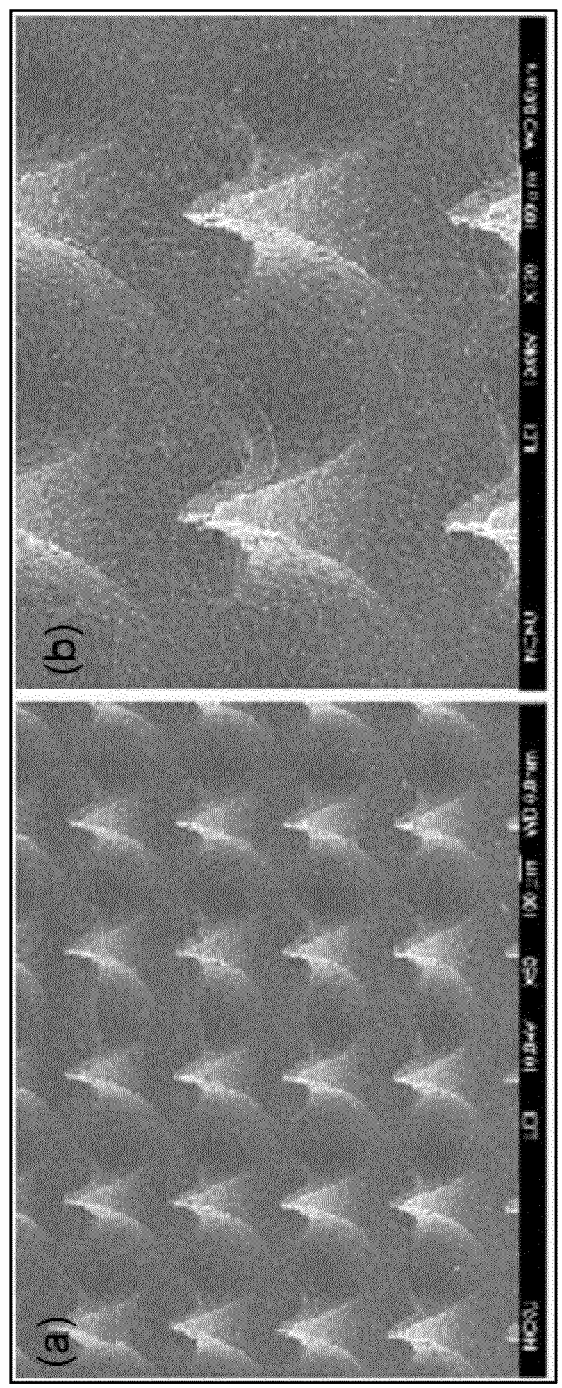
FIG. 11 is a scanning electron microscope (SEM) image of a micro-needle carrier in accordance with the present invention.

In this experiment, the method of manufacturing the transdermal drug delivery patch in accordance with the present invention is used for manufacturing a transdermal drug delivery patch with a perfect structured pyramid carrier. The micro-needle carriers have a height of approximately 400 μm, a base diameter having a width of approximately 175 μm and an aspect ratio of approximately 2.3 as shown in FIG. 11 (wherein FIGS. (a) and (b) are amplified by 50 and 120 times respectively).

Figure 12:
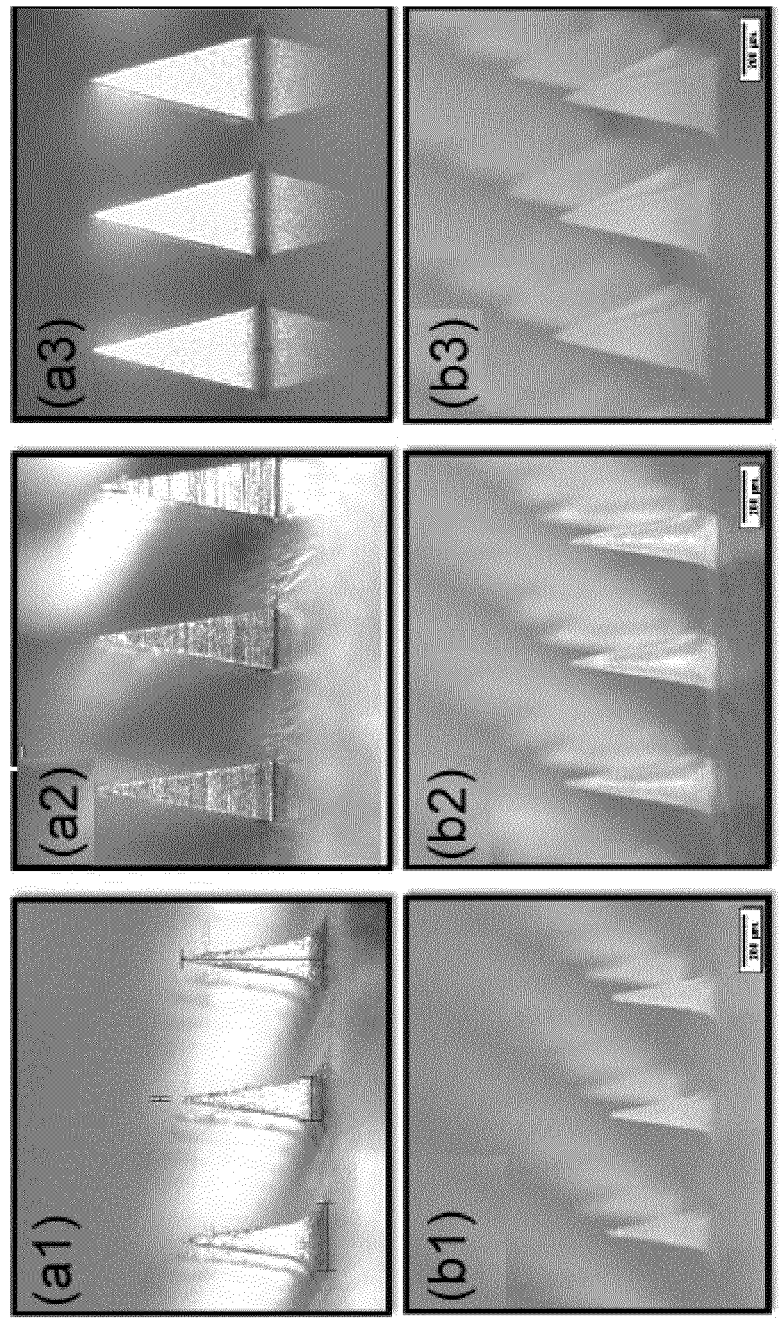
FIG. 12 shows metal structures of different micro-needle molds (a1)-(a3), and the carriers of the patches 1-3 manufactured by the micro-needle molds respectively (b1)-(b3)

Additionally, in another embodiment, the transdermal drug delivery patch of the present invention can also be produce to any scales as long as the carriers can pierce into the skin without paining. The examples of the transdermal drug delivery patch in accordance with the present invention are shown in following Table 1 and FIG. 12. In FIG. 12, FIGS. (a1)-(a3) show metal structures of different micro-needle molds, and FIGS. (b1)-(b3) show the carriers of the patches 1-3 manufactured by the micro-needle molds illustrated in FIGS. (a1)-(a3), respectively. The result reveals that the sizes and structures of the patches 1-3 are actually the same as those of the micro-needle molds.

TABLE 1

|  | Patch 1 | Patch 2 | Patch 3 |
| --- | --- | --- | --- |
| Tip radius (μm) | ~5 | ~5 | ~5 |
| Height (H, μm) | 450 | 600 | 600 |
| Base diameter (μm) | 150 | 200 | 300 |
| Aspect Ratio (A.R.) | 3 | 3 | 2 |

Figure 13:
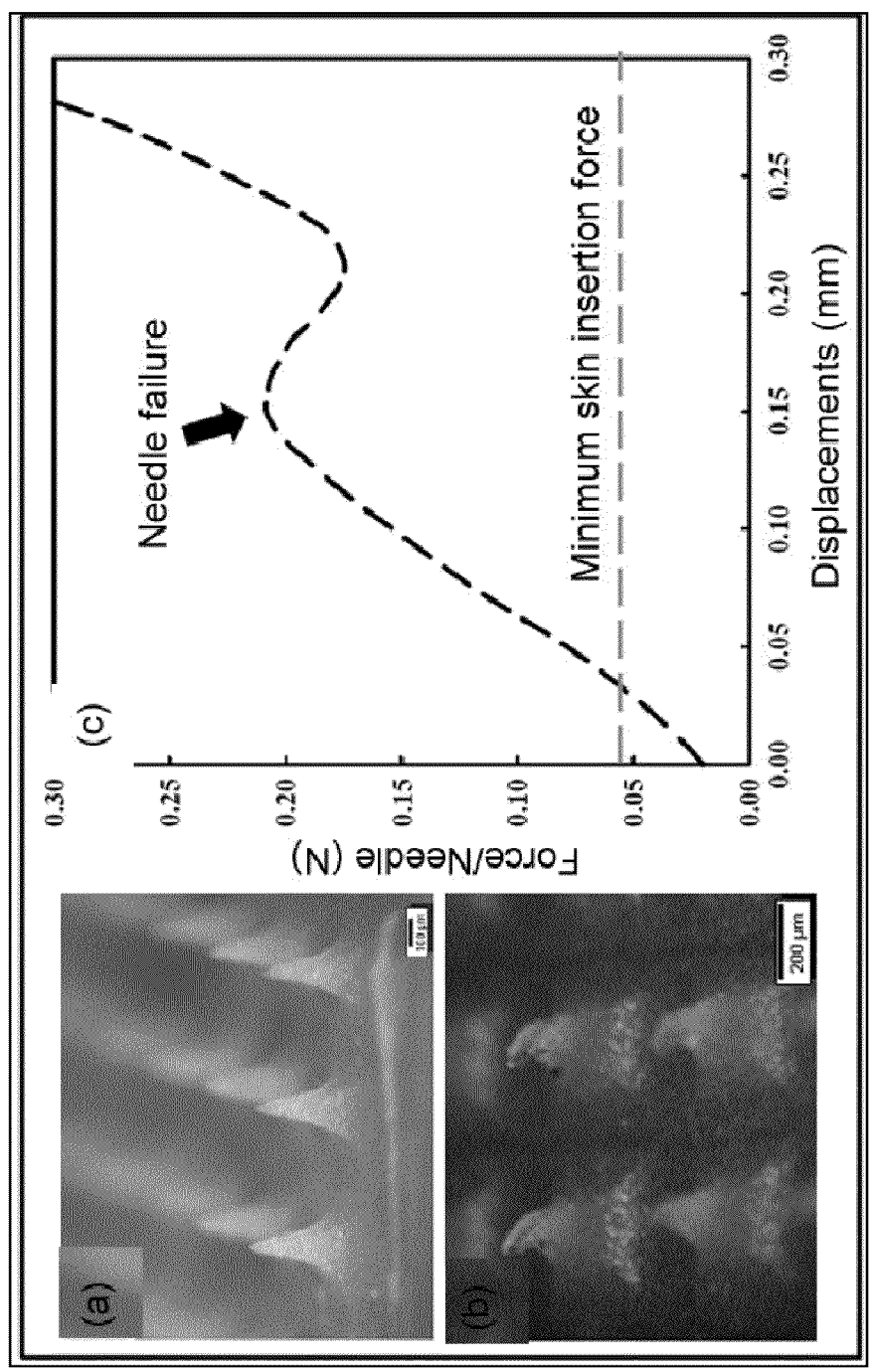
FIG. 13 shows the mechanical strength test result of a micro-needle carrier of the present invention.

As to the mechanical strength test (compression test) of the micro-needle carrier, a material testing machine is used to apply a vertically downward force to the carrier, and a quantitative analysis is performed to measure the maximum failure force of the micro-needle carrier before the micro-needle carrier is bent or deformed, and the test result is shown in FIG. 13. As shown in FIG. 13, the FIG. (a) shows an image of the carrier of the present invention before compression, the FIG. (b) shows an image of the carrier of the present invention after compression, and the FIG. (c) shows a curve of the compression and deformation of the carrier of the present invention. The results show that the carrier of the present invention can stand a failure force approximately 0.2 N/needle, and this force is much greater than the minimum penetration force (0.058 N/needle) required for a conventional micro-needle to puncture skin.

Figure 14:
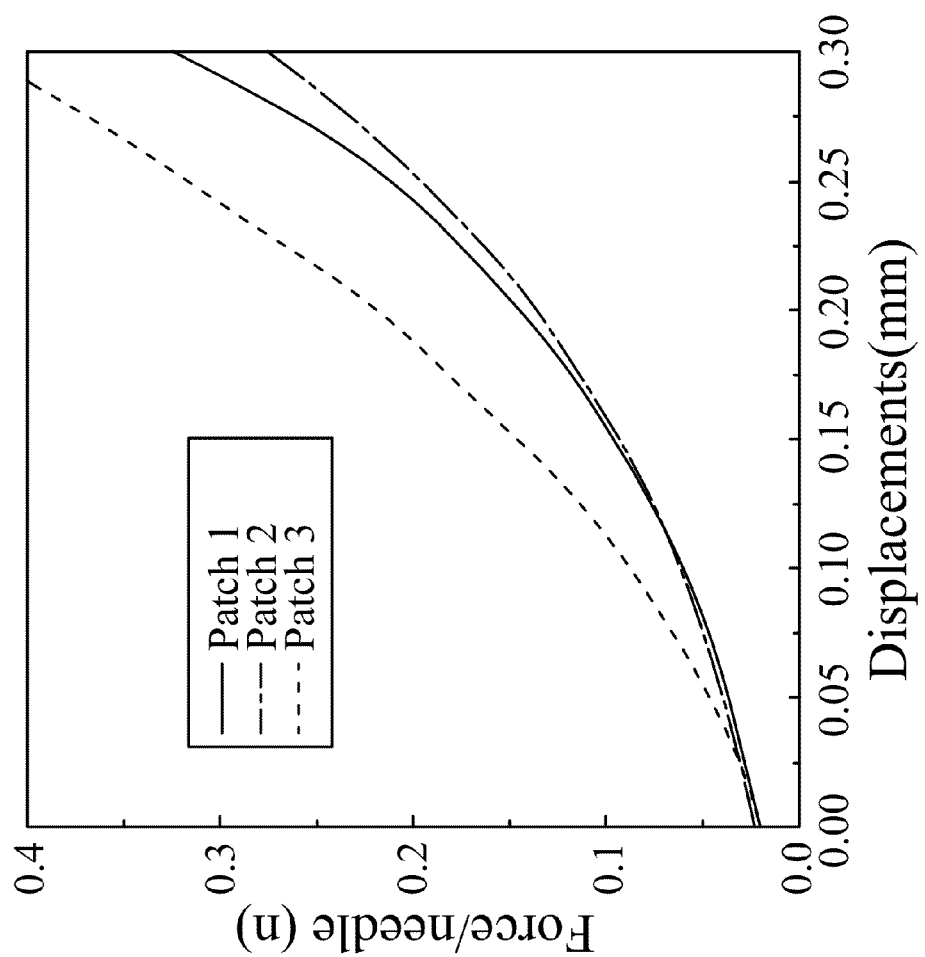
FIG. 14 shows the mechanical strength test result of micro-needle carriers of the patches 1-3 of the present invention.

The patches 1-3 are also proceeded to the mechanical strength test by the universaltesting machine of Shimadzu. The universaltesting machine applies the force with the speed of 66 mm/min to the patches 1-3. The results are shown in FIG. 14, and reveal that the mechanical strength can be increased while the transdermal drug delivery patch has the smaller aspect ratio.

Figure 15:
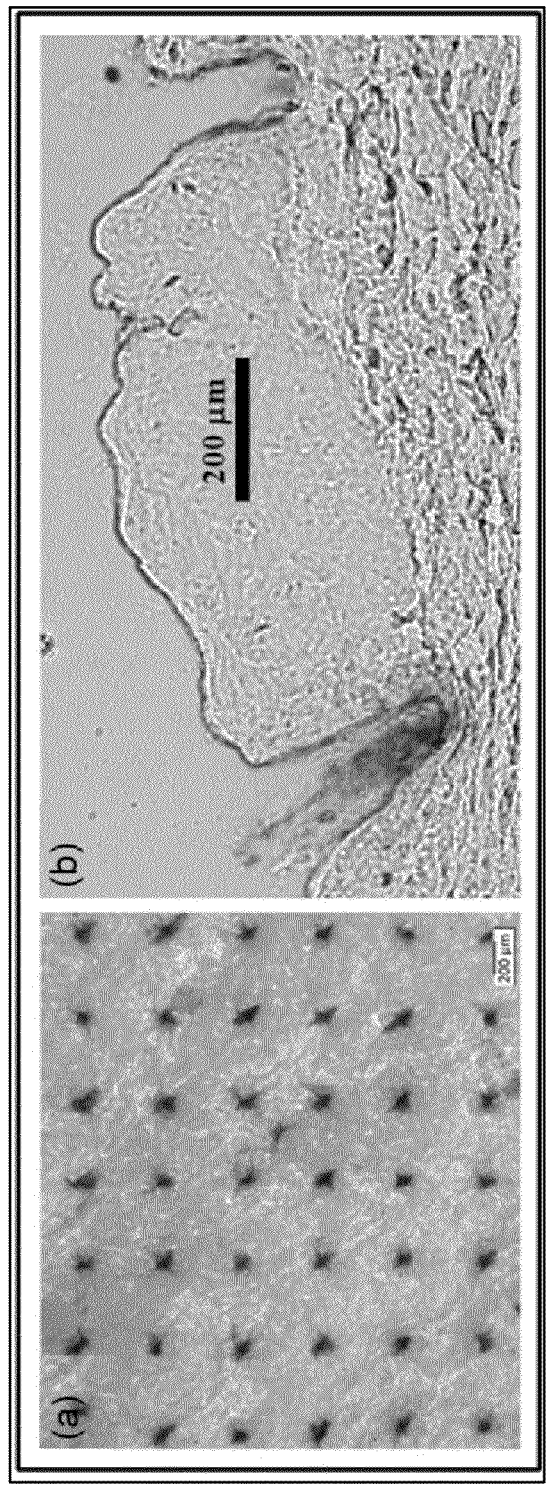
FIG. 15 shows a pigskin puncture test of a micro-needle carrier according to an embodiment of the present invention.

To further determine whether the micro-needle carrier of the present invention has the ability of puncturing skin or not, the micro-needle carrier punctures into a pigskin. The pigskin punctured with the micro-needle carrier is stained by a tissue dye, and the result shows that there are breaches formed on the surface of the pigskin caused by the puncture of the micro-needle carrier. After a blue tissue dye is penetrated into the pigskin to form an array of points in blue color, and the depth of the puncture made by the micro-needle carrier is approximately 300 μm, as shown in FIGS. (a) and (b) of FIG. 15 respectively.

Figure 16:
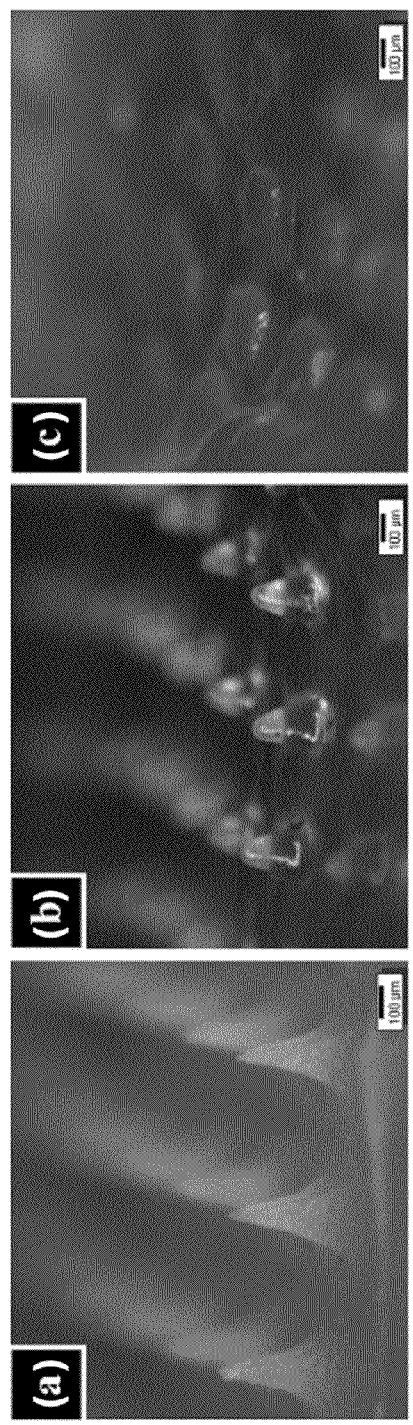
FIG. 16 shows the result of a transdermal drug delivery patch irradiated by near-IR with different time in accordance with the present invention.
Figure 17:
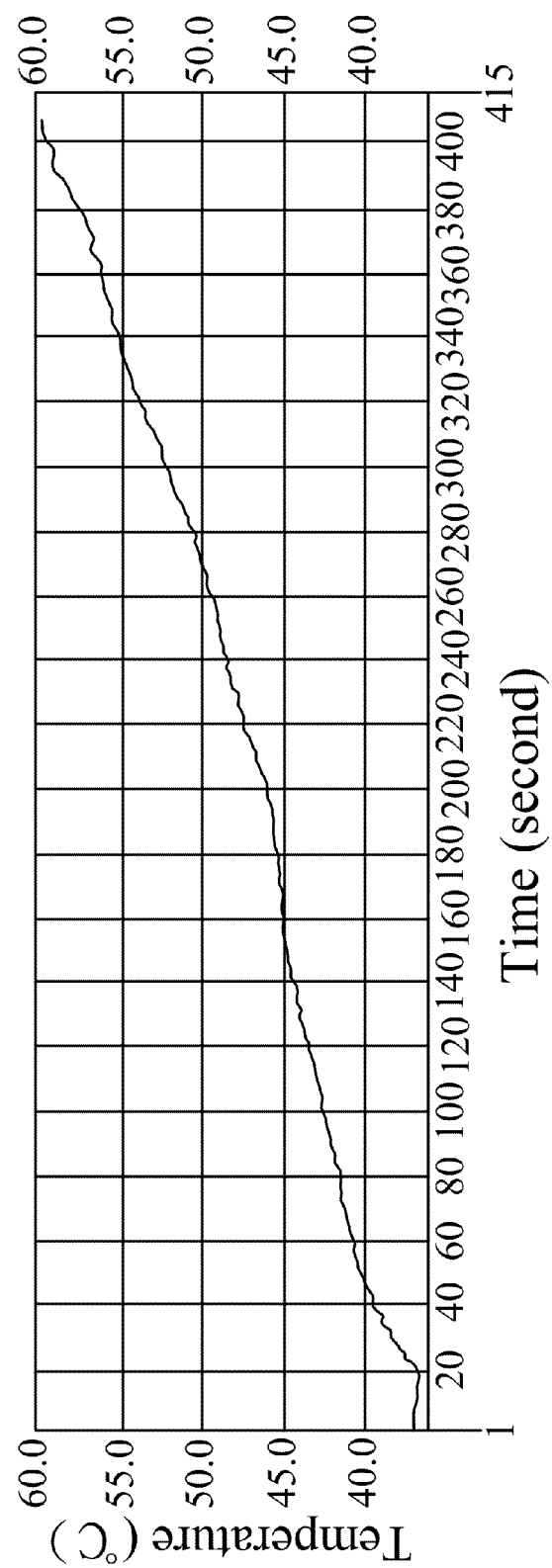
FIG. 17 shows a time versus temperature graph illustrating the temperature rise of a transdermal drug delivery patch in accordance with the present invention while irradiating via near-IR.

To further verify the concept of controlling the drug release by near-IR, the near-IR is irradiated onto a transdermal drug delivery patch in accordance with an embodiment of the present invention at different time, and the results are shown in FIG. 16. In FIG. 16, FIG. (a) shows an image of the carrier of the transdermal drug delivery patch of the present invention before the carrier is irradiated by the near near-IR, and a (pyramid shaped) micro-needle can be observed. After an irradiation of near-IR with a wavelength of approximately 808 nm and a power of approximately 730 mW takes place for 5 seconds, the carrier containing nano-particles of 0.4 wt % is melted obviously as shown in FIG. (b) of FIG. 16. After an irradiation of near-IR for 10 seconds takes place, the carrier containing nano-particles of 0.4 wt % is melted completely. Furthermore, with reference to FIG. 17, it shows a time versus temperature graph illustrating the temperature rise of a transdermal drug delivery patch in accordance with the present invention while irradiating via near-IR. The result reveals that the temperature of the transdermal drug delivery patch can be raised with the increase of the irradiation time.

Figure 18:
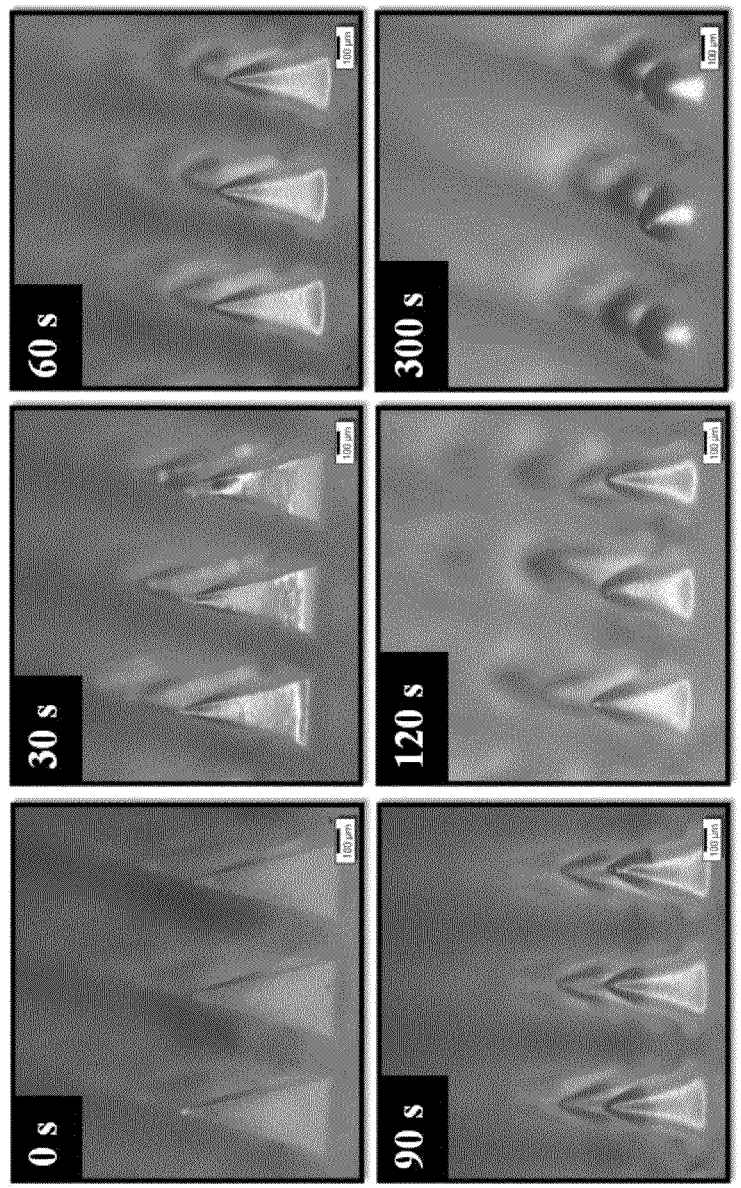
FIG. 18 illustrates that a transdermal drug delivery patch stands upside down to irradiate near-IR for 0, 30, 60, 90, 120 and 300 seconds to simulate the process of drug release after the transdermal drug delivery patch punctures into the skin.
Figure 19:
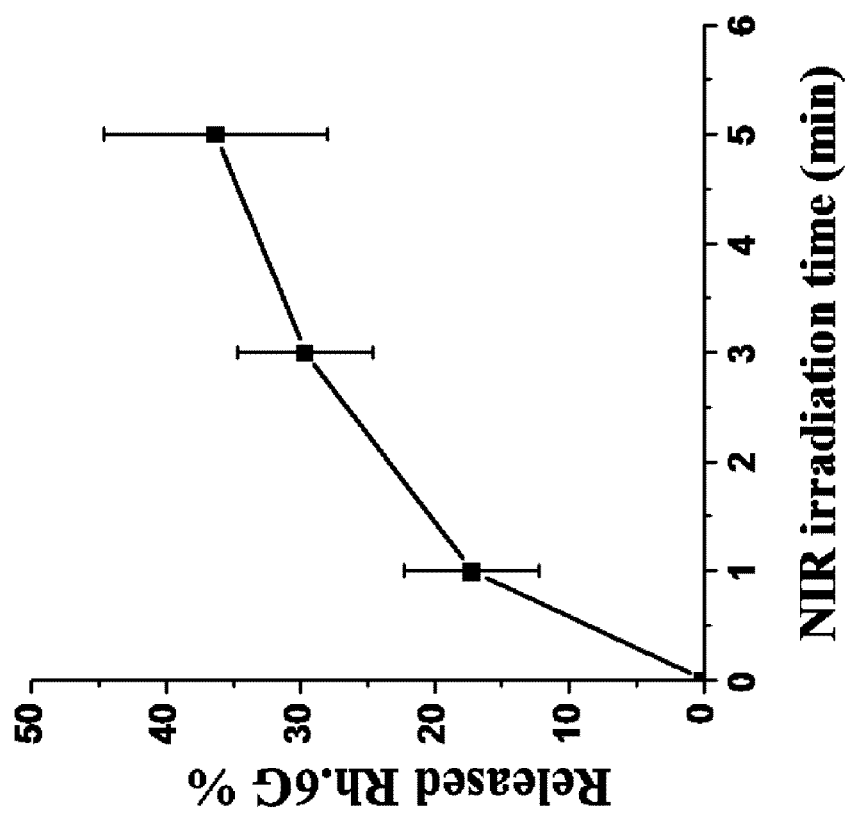
FIG. 19 illustrates the quantitative analysis of the release of the rhodamine 6G.

Moreover, the rhodamine 6G is used as a model drug and encapsulated in the micro-needle carrier of the transdermal drug delivery patch in accordance with the present invention. The result shows FIGS. 18 and 19. FIG. 18 illustrates that the transdermal drug delivery patch stands upside down to irradiate near-IR for 0, 30, 60, 90, 120 and 300 seconds to simulate the process of drug release after the transdermal drug delivery patch punctures into the skin. FIG. 19 illustrates the quantitative analysis of the release of the rhodamine 6G. The results show that the rhodamine 6G is exactly released from the micro-needle carriers of the transdermal drug delivery patch while the transdermal drug delivery patch is irradiated by the near-IR. The release quantity of the rhodamine 6G is increased with irradiation time.

Figure 20:
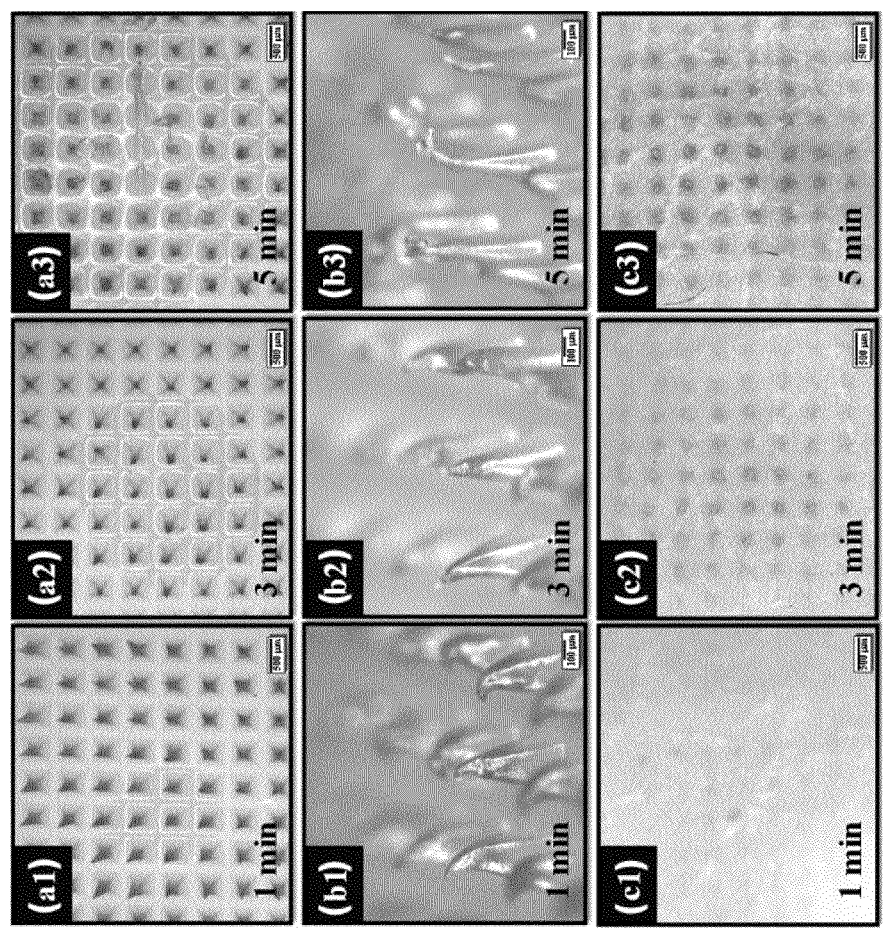
FIG. 20 illustrates top views (a1)-(a3) and side views (b1)-(b3) of the transdermal drug delivery patches, and array marks of the rhodamine 6G on the pigskin (c1)-(c3).

With reference to FIG. 20, FIGS. (a1)-(a3) show top views of the transdermal drug delivery patches irradiated by near-IR for 1, 3 and 5 minutes, respectively; FIGS. (b1)-(b3) show side views of the transdermal drug delivery patch irradiated by near-IR for 1, 3 and 5 minutes, respectively; and FIGS. (c1)-(c3) show array marks of the rhodamine 6G on the pigskin via irradiating the transdermal drug delivery patches by near-IR for 1, 3 and 5 minutes, respectively. The results reveal that when the irradiation time increases, the color on the pigskin is become darker because of the increase of the rhodamine 6G release. On the other hand, the rate of the drug release is raised with the increase of the irradiation time. Thus, the drugs encapsulated into the carriers are released with the increase of irradiation time.

The foregoing results show that the transdermal drug delivery patch of the present invention surely has the photothermal conversion effect and absorbs the near-IR to melt the carriers and release the drugs encapsulated in the carriers automatically. In addition, the transdermal drug delivery patch of the present invention can achieve the effect of controlling the drug release accurately within a constant wavelength of the near-IR by adjusting the frequency and irradiation time as needed.

In summation of the description above, the present invention can achieve the effects of controlling the drug release accurately, reducing side effects, and maximizing the treatment effect by controlling the intensity, time and frequency of the near-IR irradiation, so that the invention can be applied for diseases that require long-term treatments or medications. In addition, the transdermal drug delivery patch of the present invention is a painless minimally-invasive medical system that integrates the advantages of traditional injections and transdermal patches, uses micron-scale needles to puncture a stratum corneum of human skin without stimulating the nerve system at the dermis, and delivers a macromolecular drug into the skin effectively, such that the drug can be absorbed by capillaries and entered into target tissues or circulated in the whole body. Furthermore, since the carrier can be degraded or dissolved in human body, users need not to worry about the cracked carrier remained in the user's body forever, or the problems of using the micro-needle carrier repeatedly on purpose, and disposing used needles.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A transdermal drug delivery patch, comprising:
   a substrate;
   a carrier, disposed on a surface of the substrate, and formed by a biodegradable polymer, and having a nano-particle with a photothermal conversion effect embedded in the carrier for converting light into heat; and
   a drug, encapsulated in the carrier;
   wherein, when the carrier of the transdermal drug delivery patch is punctured into a skin, and the nano-particle of the carrier absorbs near-infrared (near-IR) radiation, the nano-particle converts the near-IR radiation into heat to melt the carrier to release the drug encapsulated in the carrier into the skin;
   wherein a shape of the carrier comprises a micro-needle, a triangular cone, a circular cone, or any shape capable of piercing the skin;
   wherein the biodegradable polymer is one selected from the collection of polycaprolactone (PCL) and methylcellulose.

2. The transdermal drug delivery patch as recited in claim 1, wherein the carrier capable of piercing the skin has a height falling within a range of 50-1200 μm.

3. The transdermal drug delivery patch as recited in claim 1, wherein the biodegradable polymer has a melting point falling within the range of 35-70° C.

4. The transdermal drug delivery patch as recited in claim 1, wherein the nano-particle comprises a metal nano-particle.

5. The transdermal drug delivery patch as recited in claim 4, wherein the metal nano-particle is one selected from the collection of a gold nano-particle, a gold nanorod, gold and silver nano hollow spheres, and a germanium (Ge) nano-particle.

6. The transdermal drug delivery patch as recited in claim 1, wherein the nano-particle is one selected from the collection of a single-walled carbon nanotube and a lanthanum hexaboride ($LaB_6$) nano-particle.

7. The transdermal drug delivery patch as recited in claim 1, wherein the drug is a pharmacological or immunoreactive reagent selected from the collection of a chemical synthetic drug, deoxyribonucleic acid (DNA), polysaccharides, a vaccine and a protein.

8. The transdermal drug delivery patch as recited in claim 1, wherein the substrate is one selected from the collection of an elastic non-woven fabric, a hydrogel glue patch, a bio-fiber, polycaprolactone, gelatin, methyl cellulose, polyethylene glycol and combinations thereof.

9. A method of utilizing a transdermal drug delivery patch according to claim 1 for controlling drug release through the use of near-IR radiation, the method comprising the steps of:
   Contacting skin with the transdermal drug delivery patch such that the carrier punctures into the skin; and
   irradiating the transdermal drug delivery patch with near-IR radiation so that the nanoparticle absorbs the near-IR radiation and converts the near-IR radiation into heat, wherein the heat melts the carrier of the transdermal drug delivery patch resulting in release of the drug from the carrier and into the skin.

10. The method as recited in claim 9, wherein a shape of the carrier comprises a micro-needle, a triangular cone, a circular cone, or any shape capable of piercing the skin.

11. The method as recited in claim 9, wherein the carrier capable of piercing the skin has a height falling within a range of 50-1200 μm.

12. The method as recited in claim 9, wherein the biodegradable polymer has a melting point falling within the range of 35-70° C.

13. The method as recited in claim 12, wherein the biodegradable polymer with the low melting point is one selected from the collection of polycaprolactone (PCL) and methylcellulose.

14. The method as recited in claim 9, wherein the nano-particle comprises a metal nano-particle.

15. The method as recited in claim 14, wherein the metal nano-particle is one selected from the collection of a gold nano-particle, a gold nanorod, gold and silver nano hollow spheres, and a germanium (Ge) nano-particle.

16. The method as recited in claim 9, wherein the nano-particle is one selected from the collection of a single-walled carbon nanotube and a lanthanum hexaboride ($LaB_6$) nano-particle.

17. The method as recited in claim 9, wherein the drug is a pharmacological or immunoreactive reagent selected from the collection of a chemical synthetic drug, deoxyribonucleic acid (DNA), polysaccharides, a vaccine and a protein.

18. The method as recited in claim 9, wherein the substrate is one selected from the collection of an elastic non-woven fabric, a hydrogel glue patch, a bio-fiber, polycaprolactone, gelatin, methyl cellulose, polyethylene glycol and combinations thereof.

19. The method as recited in claim 9, wherein the near-IR has a wavelength of 650-1300 nm.

20. The method as recited in claim 19, wherein the transdermal drug delivery patch is irradiated one or more times with an irradiation time of 0.1 second to 20 minutes each time.

* * * * *